(12) United States Patent
Choi

(10) Patent No.: US 8,501,264 B2
(45) Date of Patent: *Aug. 6, 2013

(54) PAPAYA PUREE AND USES THEREOF

(75) Inventor: Danette Vanessa Choi, Mountain View, HI (US)

(73) Assignee: Ji Kwang Inc., Hilo, HI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/336,997

(22) Filed: Dec. 23, 2011

(65) Prior Publication Data

US 2012/0100235 A1  Apr. 26, 2012

Related U.S. Application Data

(63) Continuation of application No. 10/536,617, filed as application No. PCT/IB03/05476 on Nov. 26, 2003, now Pat. No. 8,097,289.

(30) Foreign Application Priority Data

Nov. 26, 2002  (AT) .................................. A 1771/2002

(51) Int. Cl.
*A23L 1/212* (2006.01)

(52) U.S. Cl.
USPC .......................................... 426/615; 426/520

(58) Field of Classification Search
USPC .................. 426/487, 520–523, 615
See application file for complete search history.

(56) References Cited

U.S. PATENT DOCUMENTS

| 4,089,985 A | 5/1978 | Wolff |
| 5,840,356 A | 11/1998 | Swensen |

FOREIGN PATENT DOCUMENTS

| CN | 1084033 A | 3/1994 |
| CN | 1345543 | 4/2002 |
| JP | 07-067576 | 3/1995 |
| JP | 08056562 A | 3/1996 |
| JP | 10-014549 | 1/1998 |
| WO | 94/18854 | 9/1994 |

OTHER PUBLICATIONS

Attachment 1: Concetta Guiliani, Curriculum Vitae, attachment to the Declaration filed Jun. 8, 2011 in U.S. Appl. No. 10/536,617, 4 pages.*
Attachment 2: Theodore Winnick, Physicochemical Properties of the Proteolytic Enzyme From the Latex of the Milkweed, *Asclepias speciosa* Torr. Some Comparisons With Other Proteases, Oct. 9, 1939, 9 pages.*
Attachment 3: Lefo Institute—Examination report of May 21, 2004 carried out of Samples CARICOL 3105 and Papaya 3106, Apr. 2004, 2 pages.*
Chandalia, M. et al., Beneficial Effects of High Dietary Fiber Intake in Patients with Type 2 Diabetes Mellitus, May 11, 2000, The New England Journal of Medicine, vol. 324:1392-1398 No. 19, pp. 1392-1398.
Imao, K. et al. Free radical scavenging activity of fermented papaya preparation and its effect on lipid peroxide level and superoxide dismutase activity in iron-induced epileptic foci of rats, 1998, Biochemistry and Molecular Biology International, vol. 45, No. 1, pp. 11-23.
Office Action dated Aug. 10, 2010 issued on JP 2004-554848, and English translation thereof.
Dawson, E. The Medicinal Properties of the Papaya, *Carica papaya* L., Ethnobotanical Leaflets, pp. 1-3, 1998.
Starley. I. F. et al., The Treatment of Paediatric Burns Using Topical Papaya, Database Medline Online. U.S. National Library of Medicine (NLM). Bethesda, MD, US; 1999, database accession No. NLM 10563690 (Abstract) & Burns: Journal of the International Society for Burn Injuries, England, vol. 25, No. 7, pp. 636-639, 1999.
M. Gamal Abd El-Al et al., Application of Microwave Energy in the Heat Treatment of Fruit Juices, Concentrated, and Pulps, Processing, pp. 307-312, 1994.
Website print (http://recipestoday.com/recipes/shakes/papaya.htm), Jul. 14, 2003.
Website print (http://www.fruitarian.com/ao/FruitOnly.htm), Jul. 14, 2003.
International Search Report, PCT/IB03/05476, date Mar. 19, 2004.

\* cited by examiner

*Primary Examiner* — Jyoti Chawla
(74) *Attorney, Agent, or Firm* — Nath, Goldberg & Meyer; Lakshmi Rajan; Joshua Goldberg

(57) ABSTRACT

The invention relates to methods of prophylactic and/or therapeutic uses of a puree preparation from Carica papaya fruit, said puree prepared by a method comprising cooking the fruit for at least 30 minutes at normal pressure, optionally in an aqueous solution which is at least twice the volume of the fruit; cooling the cooked fruit over a period of time of at least 30 minutes in an oxygen-containing atmosphere; and homogenizing the cooled fruit to obtain a puree.

3 Claims, No Drawings

PAPAYA PUREE AND USES THEREOF

This application is a continuation application of U.S. application Ser. No. 10/536,617, filed Mar. 13, 2006, which is a National Stage of International Appl. No. PCT/IB03/05476 filed Nov. 26, 2003, which claims priority to Austrian Appl. No. A 1771/2002 filed Nov. 26, 2002, the disclosure of each hereby being incorporated herein by reference.

The invention relates to a method for preparing a puree preparation from Carica papaya fruits.

Carica papaya (melon tree) belongs to the family of Caricaceae, order Violales, and produces large, juicy and tasty fruits (papayas).

The papaya originally comes from tropical regions, where it was also cultivated. Large-scale plantations are to be found in Ceylon, Pakistan, India, Australia, East Africa and Brasilia. In Mexico and Central America there are just as many plantations, but these are substantially smaller. The tree grows up to six meters in height, the fruits may reach up to 7 kilos in weight.

In traditional medical cultures, papayas (peel, fruit pulp, seed; rarely leaves and latex) are primarily used to treat asthma, parasitoses, wound healing disorders as well as gastrointestinal problems such as diarrhoea or constipation. Their ingredients stimulate and regulate digestive activity, mitigate gastric hyperacidity, reduce excessive flatulation and promote protein cleavage.

The first written reports on possible healing effects go back to the Spaniard Oviedo (1526). Dr. Mario Rojas Alba, President of the Mexican Institute for Traditional Medicine, has been intensely engaged in exploring the healing effect of this fruit since 1996.

So far, six different enzymes have been isolated:
Papain
Chymopapain A and B
Lysozyme
Lipase
Glutamine Cyclopherase
Callose In addition, papayas are very rich in:
Pectin
Vitamins A, B, C
Essential Fatty Acids
Bioflavonoids
Potassium
Calcium
Magnesium
Phosphotides
Peptides
Amino Acids (e.g., arginine)

The glycoside carpain is said to exhibit a cardiotonic activity.

In addition to their use as food, the fruits of Carica papaya are used to produce the proteolytic enzyme papain.

Papain was used to prevent burn infections, defibrinate wounds, treat insect bites, treat oedema and inflammatory processes and promote wound healing, as well as—in low dosages—in the event of stomach upsets. Papayas are further described as being laxative and refreshing.

Papain (papaya peptidase I, EC 3.4.22.2) is obtained from the milk juice (latex) of unripe papayas, which milk juice is dried and pulverized.

The object of the present invention resides in providing an agent for the treatment of digestive disorders and a digestion-regulating agent, respectively.

The present invention, therefore, relates to a method for preparing a puree preparation from Carica papaya fruits, which is characterized by the steps of:
cooking the fruits or crushed fruits, particularly fruits in sieved form, for at least 30 minutes at normal pressure, optionally with at least twice the volume of an aqueous solution,
cooling the cooked fruits or crushed fruits for a period of at least 30 minutes in an oxygen-containing atmosphere,
optionally crushing, mixing and straining the cooled fruits or crushed fruits until a homogenous puree is obtained.

In a surprising manner, a puree thus prepared under consideration of the appropriate cooking and cooling times turned out to be particularly suitable for the treatment of digestive disorders; a property that will not occur, or occur only to an extremely slight extent, if said cooking and cooling times are not observed.

The minimum period of 30 minutes refers to cooking conditions at normal pressure, yet the minimum cooking time will be accordingly reduced if the raw material is cooked under pressure.

The fruit cooking according to the invention—as a function of the water content of the employed fruits—is preferably performed with at least twice the volume of an aqueous solution and, preferably, with about four times said volume. This embodiment is particularly suitable if whole fruits are cooked, or if crushed fruits having low water contents are used. Here, too, applies that the necessary amount of water is to be reduced to a fraction when cooking takes place in a closed container (under pressure), since otherwise the final product will be too diluted with at least twice the amount of water. Cooking is usually carried out upon addition of conventional tap water without any additives. In a preferred manner, cooking is carried out for at least 2 hrs, preferably for at least 3 hrs and, in particular, for at least 5 hrs. The cooling process is, for instance, realized by interrupting any further heat energy input or by taking the containers in which the fruits were cooked from the cooking site to a place at room temperature. As already pointed out above, said cooling process is likewise very important for the generation of the digestion-regulating properties of the puree according to the invention and should last for at least 30 min, preferably for at least 5 hrs and, even more preferred, for at least 6 hrs (or 5 to 7 hrs, respectively); yet, cooling times of 10 hrs and more are also feasible. The supply of oxygen is important during the cooling process, any operation preferably taking place under air supply.

In a preferred manner, citric acid may be added during the preparation of the puree, particularly in the crushing, mixing and straining step, in order to enhance its storage quality. Likewise preferred is the subsequent pasteurization of the obtained puree under usual food-technological conditions.

In order to obtain a final product which appears even more appetizing in terms of consistency and form, and can be taken more easily, the fruits may be peeled and stoned prior to cooking. On that occasion, the fruits may also be crushed straight-away prior to the cooking process, e.g. by sieving.

The best results will be obtained with Carica papaya fruits that are half-ripe to ripe. The state of ripeness of papaya fruits may be defined by way of their colors: unripe fruits have 100% green skins, half-ripe fruits are 50-75% yellow, ripe fruits are 80-100% yellow.

According to a central aspect, the present invention relates to the use of a puree preparation from Carica papaya fruits, which is producible by the method according to the invention, for the production of an agent for the treatment of digestive disorders. As pointed out above, the product prepared according to the invention in a surprising manner is particularly well suited for the treatment of digestive disorders and, in particular, for the treatment of chronic constipation, flatulation and irritable colon syndrome, which is all the more surprising since that aptness does not primarily go back to the nature of Carica papaya fruits, but to the special mode of preparation of the puree according to the invention.

According to another predominant aspect, the present invention relates to the use of the puree prepared according to the invention in the non-therapeutical field, e.g., for improving the digestion process in persons who are actually healthy and do not suffer from digestive disorders, for instance in the form of nutritional additives or supplements.

The water content of the preparation according to the invention may preferably range from 9 to 90%, the respective indication being of particular relevance to the adjustment of the water content. In this respect, a water content ranging from 60 to 85% and, in particular, 70 to 80% has turned out to be particularly preferred, since such a water content not only yields high efficacy, but also offers substantial advantages of administration:

A special aspect of the present invention relates to the puree preparation from Carica papaya fruits itself, which is obtained by the method according to the invention. As pointed out above, said preparation is particularly effective on account of the special mode of its preparation and, in particular, the cooking and cooling times applied, and, as a result, is especially suitable for the indications reported in accordance with the invention.

Thus, tree-ripe picked fruits, for instance, have a water content of around 88% and a sugar content of 8 to 12%. If they were used to produce a 1:1 product, twice the dose would, for instance, have to be administered with the dosage indications listed below in order to provide improvement in the case of constipation, i.e., actually four tablespoons twice, or 40 ml twice, instead of two tablespoons twice, or 20 ml twice, respectively. At a concentration of about 2:1, based on tree-ripe picked fruits, which concentration is particularly preferred, a final product having a water content of about 77% and a sugar content of 16 to 24% will, thus, result.

It is precisely the sugar content which too constitutes an essential product parameter of the puree according to the invention. Said sugar content preferably ranges from 5 and 40%, in a particularly preferred manner from 10 to 30% and, in particular, 12 to 26%. When treating diabetic patients or diabetes-endangered patients, for instance in geriatrics, special care will, of course, have to be taken in the adjustment of the sugar content.

The effectiveness of the preparation obtainable according to the invention is particularly surprising, above all because of the fact that the production method also involves a long-lasting cooking process. This is remarkable primarily in view of the activity in improving the digestion process and, in particular, chronic constipation, since all known publications relating to the positive digestion-promoting action of papaya preparations are founded on the general digestion-promoting action of the enzyme papain, or based on the action of papain. It has, however, been proved that papain is cleaved, and becomes ineffective, at treatment temperatures rising to above 85° C. such that the the production method according to the invention runs totally counter to that prior art, being in contradiction to the same. Consequently, the results indicated in the examples, of the clinical studies demonstrating the effects inter alia in the case of chronic constipation and chronic diarrhoea have all the more been surprising bearing in mind the obvious papain-cleaving mode of production.

The preparation obtainable according to the invention exhibits excellent prophylactic and therapeutic properties, and, in particular, special immune-strengthening and wound-healing-promoting effects, particularly with ulcus cruris, as well as effects for the reduction of the insulin demand in diabetic patients, for increasing vitality and for improving conditions of patients suffering from Parkinson's disease have been observed in the context of clinical studies carried out with the preparation obtainable according to the invention. These indications, therefore, definitely constitute an outstanding aspect of the present invention—in addition to the treatment of digestive disorders.

Dosages may strongly vary as a function of the respective clinical characteristics of the disease to be treated. Thus, the treatment of chronic diarrhoea, for instance, requires a substantial lower dosage than the treatment of constipation, in order to induce sufficient activity, for which reason also the water content, for instance, for the treatment of chronic constipation is adjusted more in the lower range (e.g., between 70 and 85%), whereas a higher water content and also a lower dosage are applied with agents used to treat diarrhoea.

The adjustment of the water content may be realized in a simple manner in the context of the cooking procedure. Depending on the water content of the fruits used, water may be added or not in the method according to the invention; if, for instance, the papayas are subjected to the cooking procedure already in crushed (mashed, sieved, etc.) form, the addition of water may preferably be omitted. That mode of production has turned out to be or particular advantage in the on-site preparation of the papaya puree according to the invention, since these fruits will usually have elevated water contents when harvested.

The invention will be explained in more detail by way of the following examples to which it is, of course, not limited.

EXAMPLES

1. Preparation of the Puree According to the Invention From Carica Papaya Fruits 100 kg papaya fruits having an at least 20% yellow portion in the skins are peeled and stoned, filled into a 500-liter cooking vessel and supplemented with 300 liters of tap water. With the vessel open, the fruits are subsequently cooked with water for 3 hrs and then allowed to cool, opened, at room temperature for 6 hrs.

After cooling, the cooked material is supplemented with citric acid until the pH drops to about 3.8% (around 600 g).

After this, the cooled cooked material is mixed or strained to a fine puree, filled in 1-liter glasses, closed and pasteurized.

2. Larger-Scale Production of the Puree According to the Invention

For the production of larger quantities and, in particular, for on-site production (in the country of origin of papayas), the following preprocessing has proved to be advantageous:

The fruits are washed, subsequently mechanically freed of their skins and stones (the fruits are driven through a sieve already at this stage in order to remove the stones, hence straining after cooking may be obviated). After this, citric acid is added to adjust the pH to between 3.5 and 5.0 and, in particular, 3.8 and 4.4, whereupon the puree is pasteurized and sterile-filled into barrels. It can thus be dispatched by air or ocean freight.

If semi-finished products from half-ripe to ripe papayas have water contents higher than those of the fruits available on European markets, e.g. around 88%, it is not necessary at all to add water for cooking, particularly where crushing has already been effected prior to cooking. In order to reach the consistency and concentration desired for product-technical reasons, even the semi-finished product may be concentrated by the cooking process to such an extent that the water content drops to about 77% and the sugar content rises to about 16% (the latter amounting to about 5% in unripely picked fruits and ranging from about 8 to 12% in fruits picked in the half-ripe to ripe states). In practice, this is usually realized in that one liter of "crude puree" is concentrated to about half a liter of "ready-made puree".

After the cooking and cooling procedures, which are essential to the effect and are not varied, there are two preferred ways of packaging:

A) Glass Packaging

In this case, the puree concentrate (according to the ordinance on food stuffs, a concentrate is referred to as such from a concentration of 2:1) is filled into glass bottles and subsequently pasteurized.

B) Pillow Bags or Stickpacks

The puree concentrate is portioned into stickpacks (of 20 ml each), welded and subsequently pasteurized as well, or aseptically filled at once in the hot state.

3. Study on the Effectiveness of the Papaya Preparation According to the Invention in Geriatric Patients Suffering From Chronic Constipation 3.1. Description of the Preparation Under Study Tree-ripe picked papaya fruits are peeled and stoned and subsequently cooked with twice the volume of an aqueous solution for between 30 min and 5 hrs. After this, the dried fruits are cooled in an oxygen-containing atmosphere for a period of at least 30 min, strained and supplemented with citric acid. For the study, the preparation was filled into glasses and pasteurized, after opening the glasses were stored in the refrigerator.

3.2. Study Design

Forty patients or residents of a geriatric center, who were mainly immobile, were included in the study. All of them had the medical diagnosis of chronic constipation. All of them received laxatives once a day to at least thrice a week. More than 95% received Macrogol (Movicol®).

Excluded were patients or residents who fulfilled at least one of the following criteria:
known malignant tumor
stoma
blood in the stool
higher-grade heart insufficiency
experiencing morphine therapy The course of the study was divided into a preliminary period of 19 days, an examination period 1 of 35 days, during which the preparation according to the invention was administered twice a day (2 tbsp. before breakfast with some water, 2 tbsp. before lunch with some water), an examination period 2 of 19 days, in which the preparation according to the invention was reduced to an administration in the morning (2 tbsp. before breakfast with some water).

During the entire examination period, the stool behavior of the patients was documented extremely precisely on special documentation sheets.

The escape therapy, i.e., where no defaecation occurred despite the administration of the study preparation, comprised 2 Microklist® administered on the third day without defaecation and 1 Relaxyl® administered on the fourth day without defaecation.

3.3. Study Course

Forty patients or residents who complied with the above-defined criteria were included in the study.

In the preliminary phase, 8 patients were excluded from the study. The reasons were lacking compliance, the dislike of the taste of the preparation according to the invention or insufficient control of defaecation, since some of them used the toilet sometimes on their own despite their limited mobility.

In the examination phase 1, 13 patients (of a remaining total of 32) showed an improvement in the degree of constipation (quotient from the number of days without defaecation divided by the number of days with defaecation). 0 means daily defaecation, 1 means 50% of the days without defaecation, etc.

5 patients showed a slight increase in defaecation-free days as compared to the preliminary phase, yet showed clear improvement in the examination phase 2 over the preliminary phase. 11 patients showed a deterioration of the degree of constipation. 4 patients exhibited the same degree of constipation as in the preliminary phase—thus did not show any deterioration either.

In the examination phase 2, a total of 18 patients were continued to be observed. Of these, 13 patients showed a further continuous decrease of the constipation quotient despite a dose reduction. In 3 patients, a progredient increase in the constipation quotient as compared to the preliminary phase occurred (possibly, a medicamentous interaction was to be taken into consideration here, since those patients received several psycho-pharmaceuticals). In those cases, separate examinations at higher dosages of the study preparation are recommended. One patient had stool every day during the entire study period. One patient experienced a deterioration in the examination phase 2 (dose reduction) as compared to the examination phase 1, yet did clearly better than in the preliminary phase.

3.4. Summary

A significant effect on the improvement of stool habits without any intervention of laxatives could be demonstrated by this prospective study, which was carried out in 40 patients or residents of a geriatric department (immobility, multimorbidity) using a so-called nutritional supplement, namely a papaya pulp form prepared according to the invention (=CARICOL®). Special mention should be made of the course of the constipation degree in a female patient having a PEG probe, to whom the preparation was administered by the aid of a so-called Alexander syringe (by which dosages could be most accurately observed): preliminary phase 1.38, $1^{st}$ examination phase 0.4, $2^{nd}$ examination phase 0.

4. Use of the Papaya Puree According to the Invention for the Treatment of Chronic Constipation The papaya puree according to the invention regulates or improves the digestion process, particularly in the event of diarrhoea, constipation (even chronic constipation), flatulation or irritable colon syndrome.

To this end, 2 tablespoons of papaya puree are each taken with the meals in the morning and at lunch. In most cases, the digestion-regulating effect will set in already on the following day or two days later.

5. Study on the Effectiveness of the Papaya Preparation According to the Invention in Geriatric Patients Suffering From Chronic Diarrhoea Study Design Ten patients or residents of the nursing station of a rooming house for pensioners, who were mainly suffering from diarrhoea, were covered by the application observation.

Excluded were patients or residents who fulfilled at least one of the following criteria:
known malignant tumor
stoma
blood in the stool After a preliminary period of 2 weeks with 4 patients, and 3.5 weeks with 6 patients, CARICOL® (papaya preparation according to the invention) was administered to the patients in two therapy phases. In phase 1, CARICOL® was administered twice a day in single concentrations for 3.5 weeks (in 6 patients) and 5 weeks (in 4 patients), respectively. Their stool behaviors were documented most precisely.

After this, the therapy was suspended for three weeks.

In the subsequent phase 2, the administration of CARICOL® was continued with twice the concentration twice a day for 6 weeks.

Dosage

Phase 1: Single concentration of CARICOL® at a daily dose of 40 ml, which corresponds to the amount of 2×2 tablespoons. Intakes each occurred shortly before the meals in the morning and at lunch.

Phase 2: Double concentration of CARICOL® at a daily dose of 40 ml, which corresponds to the amount of 2×2 tablespoons. Intakes each occurred shortly before the meals in the morning and at lunch.

Documentation

The anamnestic data of each participating resident, such as the name, age, sex, operations, diagnoses and current medication, were listed in a special data sheet.

Daily administrations of CARICOL® and stool forms were documented in socalled stool sheets.

In the recordings, differentiation was made between the following stool forms:
O=no stool
I=normal stool
+=traces of stool
~=liquid
§=pasty
H=hard Results At the beginning of the preliminary phase, the average portion of pasty/liquid stool was 4 days/week, that of normal stool was 2.5 days/week.

Already shortly after the onset of the therapy phase, a balance between pasty/liquid stool and normal stool could be reached.

In the final week of phase 1, the average portion with normal stool reached about 5 days/week and the average portion with pasty/liquid stool could be reduced to about 1 day per week.

In that period of observation of phase 1, a majority of days with pasty/liquid stools could be reversed into a majority of days with normal stools in all 10 subjects.

After three weeks of discontinuation, the average portion of normal stools in phase 2 at the beginning of the therapy was only 3.8 days/week (after 5 at the end of phase 1), that of pasty/liquid stools was 2.7 days/week.

In the final week of phase 2, the average portion with normal stool reached about 3.1 days/week and the average portion of pasty/liquid stool could be reduced to about 1.8 days a week.

A comparison between phases 1 and 2 demonstrates:

In geriatric patients, the stool tends to resume its original form after discontinuation of the therapy.

In the case of chronic diarrhoea, the therapy in phase 1 with the single CARICOL® concentration yields better results than the double-concentration therapy of phase 2.

In phase 1, the time from the beginning of the therapy until the attainment of a response was substantially shorter than in phase 2, and normal stool in phase 1 reached substantially higher values than in phase 2 (the gap between normal stool and pasty/liquid stool having opened substantially more widely in phase 1 than in phase 2).

Also, in the observation period of phase 2 using twice the concentration of CARICOL® the majority of days with pasty/liquid stool could be reversed into a vast majority of days with normal stool only in 8 of the 10 subjects.

SUMMARY

A significant effect on the improvement of stool habits with chronic diarrhoea could be demonstrated by this application observation, which was carried out in 10 patients or residents of a geriatric department (multimorbidity, partial immobility) using a so-called nutritional supplement, namely a papaya pulp form prepared according to the invention (=CARICOL®).

Special mention should be made of the surprising, remarkably far-reaching improvement during intake, of an ulcus cruris that has existed for years in one of the patients observed.

6. Further Study on the Effectiveness of the Papaya Puree According to the Invention in Geriatric Patients Suffering From Chronic Constipation Study Desgin Eighteen patients of a geriatric department, who were mainly, immobile, were included in the study. All of them had the medical diagnosis of constipation and received laxatives daily to several times a week.

Excluded were patients or residents who fulfilled at least one of the following criteria:
known malignant tumor
stoma
blood in the stool
higher-grade heart insufficiency
existing morphine therapy The course of the study was divided into a preliminary period of 25 days, an examination period 1 of 35 days, during which the preparation according to the invention was administered twice a day (3 tbsp. before breakfast with some water, 3 tbsp. before lunch with some water), an examination period 2 of 21 to 28 days, in which the preparation according to the invention was reduced to an administration in the morning (2 tbsp. before breakfast with some water).

During the entire examination period, the stool behaviors of the patients were documented extremely precisely on special documentation sheets.

The escape therapy, i.e., where no defaecation occurred despite the administration of the study preparation, comprised 2 Lecicarbon® administered on the third day without defaecation and 2 Microklist® administered on the fourth day without defaecation.

Study Course

Eighteen patients who complied with the above-defined criteria were included in the study.

In the examination phase 1, 12 patients (out of a total of 18) showed an improvement in the degree of constipation (quotient from the number of days without defaecation divided by the number of days with defaecation. 0 means daily defaecation, 1 means 50% of the days without defaecation, etc.) as compared to the preliminary phase. Two patients showed a slight increase in stool-free days as compared to the preliminary phase, yet experiences a marked improvement in examination phase 2 over the preliminary phase. Four patients showed a deterioration of the degree of constipation.

4 patients showed a deterioration of the degree of constipation.

In the examination phase 2, a remaining total of 14 patients continued to be observed. Of these, 5 patients showed a further continuous decrease of the constipation quotient despite a dose reduction. 3 patients showed no change relative to examination phase 1 despite a dose reduction to 2 tablespoons once before breakfast (one third of the dose) in the examination phase 2. In the examination phase 2 (dose reduction), 3 patients experienced a deterioration as against the examination phase 1, yet a marked improvement over the preliminary phase. In 3 patients, an increase in the degrees of constipation relative to the preliminary phase occurred. In those cases, separate examinations at higher dosages of the study preparation are recommended.

In addition to the development of the degree of constipation, the course of the interventions is also noteworthy. If an escape medication still had to be administered 21 times during the first week of the preliminary phase, interventions could be reduced to 9 in the final week of examination phase 1 and to 5 and 3, respectively, in the final weeks of examination phase 2 (dose reduction).

Summary

A significant effect on the improvement of stool habits without any intervention of laxatives could be demonstrated by this prospective study, which was carried out in 18 patients of a geriatric department (immobility, multimorbidity) using a so-called nutritional supplement, namely a papaya pulp form prepared according to the invention (=CARICOL® ).

7. Additional Clinical Observations in the Context of the Performed Tests

The following clinical observations were reported in the context of the studies carried out under 3.-6. above:

A patient who did not want to get up for quite a long time and was very absent mentally, regained new energy after having taken the agent according to the invention for some days, he wished to get out of bed and his speech became clearer again.

Various treatments including skin transplantations did not lead to any improvement in a woman who had been suffering from an open foot ulcer (ulcus cruris) for more than a year. Although that woman did not experience any digestion problems, she insisted on taking the agent according to the invention and did so very consistently over three months with the foot having been healed as a result.

In a female diabetic, an open foot sore improved considerably, and less insulin had to be injected, after a few weeks of administration of the agent according to the invention.

The motor functions of a patient suffering from Parkinson's disease could be visibly improved after a therapy with the papaya extract prepared according to the invention.

From the above observations in the context of the studies carried out on the indications "chronic constipation" and "chronic diarrhoea", it could, therefore, be taken that the agent according to the invention definitely also had positive effects on metabolism, the body's defence forces, the state of patients suffering from Parkinson's disease, wound healing and even blood circulation.

The invention claimed is:

1. A method for reducing the insulin requirement in diabetics, comprising administering a puree preparation prepared from Carica papaya fruits by a method comprising:
    cooking the Carica papaya fruits in an aqueous medium for at least 30 minutes at normal pressure, wherein the volume of the aqueous medium is at least twice of the water content of the fruits;
    cooling the cooked Carica papaya fruits for a period of at least 30 minutes in an oxygen containing atmosphere; and
    homogenizing the cooled Carica papaya fruits by at least one of crushing, mixing and straining the mixture,
    wherein the water content of the finished puree preparation ranges from 60-85% by weight and the puree preparation comprises active papain in an amount effective to achieve prophylactic and/or therapeutic properties.

2. A method for increasing vitality, comprising administering a puree preparation prepared from Carica papaya fruits by a method comprising:
    cooking the Carica papaya fruits in an aqueous medium for at least 30 minutes at normal pressure, wherein the volume of the aqueous medium is at least twice of the water content of the fruits;
    cooling the cooked Carica papaya fruits for a period of at least 30 minutes in an oxygen containing atmosphere; and
    homogenizing the cooled Carica papaya fruits by at least one of crushing, mixing and straining the mixture,
    wherein the water content of the finished puree preparation ranges from 60-85% by weight and the puree preparation comprises active papain in an amount effective to achieve prophylactic and/or therapeutic properties.

3. A method for improving the condition of patients suffering from Parkinson's disease, comprising administering a puree preparation prepared from Carica papaya fruits by a method comprising:
    cooking the Carica papaya fruits in an aqueous medium for at least 30 minutes at normal pressure, wherein the volume of the aqueous medium is at least twice of the water content of the fruits;
    cooling the cooked Carica papaya fruits for a period of at least 30 minutes in an oxygen containing atmosphere; and
    homogenizing the cooled Carica papaya fruits by at least one of crushing, mixing and straining the mixture,
    wherein the water content of the finished puree preparation ranges from 60-85% by weight and the puree preparation comprises active papain in an amount effective to achieve prophylactic and/or therapeutic properties.

* * * * *